(12) United States Patent
Nobis et al.

(10) Patent No.: US 7,959,642 B2
(45) Date of Patent: Jun. 14, 2011

(54) MEDICAL INSTRUMENT HAVING A NEEDLE KNIFE

(75) Inventors: Rudolph H. Nobis, Mason, OH (US); Ifung Lu, Skokie, IL (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 0 days.

(21) Appl. No.: 11/435,376

(22) Filed: May 16, 2006

(65) Prior Publication Data
US 2007/0270895 A1    Nov. 22, 2007

(51) Int. Cl.
*A61B 17/32*    (2006.01)
(52) U.S. Cl. ........................................ 606/170
(58) Field of Classification Search .............. 606/170, 606/39, 45, 130, 159, 171, 167; 604/95.04, 604/528
See application file for complete search history.

(56) References Cited

U.S. PATENT DOCUMENTS

| | | |
|---|---|---|
| 2,976,865 A | 3/1961 | Shipley |
| 3,470,876 A | 10/1969 | Barchilon |
| 3,521,620 A | 7/1970 | Cook |
| 3,791,387 A | 2/1974 | Itoh |
| 3,799,151 A | 3/1974 | Fakaumi et al. |
| 3,805,791 A | 4/1974 | Seuberth et al. |
| 4,102,478 A | 7/1978 | Samoilov |
| 4,326,530 A | 4/1982 | Fleury, Jr. |
| 4,493,320 A | 1/1985 | Treat |
| 4,619,247 A | 10/1986 | Inoue et al. |
| 4,638,802 A | 1/1987 | Okada |
| 4,735,194 A | 4/1988 | Stiegmann |
| 4,739,768 A | 4/1988 | Engelson |
| 4,758,750 A | 7/1988 | Itagaki et al. |
| 4,791,963 A | 12/1988 | Gronert et al. |
| 4,884,557 A | 12/1989 | Takehana et al. |
| 4,890,602 A | 1/1990 | Hake |
| 4,893,613 A | 1/1990 | Hake |
| 4,930,494 A | 6/1990 | Takehana et al. |
| 4,963,147 A * | 10/1990 | Agee et al. .................... 606/170 |
| 5,002,041 A | 3/1991 | Chikama |
| 5,035,696 A | 7/1991 | Rydell |
| 5,066,295 A | 11/1991 | Kozak et al. |
| 5,078,716 A | 1/1992 | Doll |
| 5,171,314 A | 12/1992 | Dulebohn |
| 5,201,732 A | 4/1993 | Parins et al. |

(Continued)

FOREIGN PATENT DOCUMENTS

DE    4408730    9/1995

(Continued)

OTHER PUBLICATIONS

Ginsberg, G.G., "Colonoscopy with the variable stiffness colonoscope," Gastrointestinal Endoscopy, vol. 58, No. 4 (2003).

(Continued)

*Primary Examiner* — Gary Jackson
*Assistant Examiner* — Lindsey Bachman (57) ABSTRACT

A medical instrument includes a flexible sheath, a pivot base, a medical needle knife base, a medical needle knife, and a handpiece. The flexible sheath has a distal sheath portion insertable within a patient and has a proximal sheath portion. The pivot base is attached to the distal sheath portion. The needle knife base is pivotally connected to the pivot base and has a passageway. The medical needle knife is extendable from the passageway and is retractable within the passageway. The handpiece is connected to the proximal sheath portion and includes a manually-operated articulation control operatively connected to the needle knife base for pivoting the needle knife base with respect to the pivot base.

4 Claims, 9 Drawing Sheets

U.S. PATENT DOCUMENTS

| | | | |
|---|---|---|---|
| 5,201,741 | A | 4/1993 | Dulebohn |
| 5,250,060 | A * | 10/1993 | Carbo et al. ............... 606/159 |
| 5,293,869 | A | 3/1994 | Edwards et al. |
| 5,322,505 | A * | 6/1994 | Krause et al. ................ 604/24 |
| 5,342,299 | A * | 8/1994 | Snoke et al. ............. 604/95.04 |
| 5,346,504 | A | 9/1994 | Ortiz et al. |
| 5,351,692 | A | 10/1994 | Dow et al. |
| 5,353,807 | A | 10/1994 | DeMarco |
| 5,397,304 | A | 3/1995 | Truckai |
| 5,409,453 | A | 4/1995 | Lundquist et al. |
| 5,431,671 | A * | 7/1995 | Nallakrishnan ............. 606/167 |
| 5,433,721 | A | 7/1995 | Hooven et al. |
| 5,441,499 | A * | 8/1995 | Fritzsch ..................... 606/45 |
| 5,482,029 | A | 1/1996 | Sekiguchi et al. |
| 5,522,829 | A * | 6/1996 | Michalos ..................... 606/170 |
| 5,531,664 | A | 7/1996 | Adachi et al. |
| 5,531,686 | A | 7/1996 | Lundquist et al. |
| 5,542,948 | A | 8/1996 | Weaver et al. |
| 5,618,294 | A | 4/1997 | Aust et al. |
| 5,628,719 | A | 5/1997 | Hastings et al. |
| 5,706,827 | A | 1/1998 | Ehr et al. |
| 5,728,044 | A | 3/1998 | Shan |
| 5,749,828 | A | 5/1998 | Solomon et al. |
| 5,752,961 | A | 5/1998 | Hill |
| 5,776,080 | A | 7/1998 | Thome et al. |
| 5,792,165 | A * | 8/1998 | Klieman et al. ............. 606/170 |
| 5,810,715 | A | 9/1998 | Moriyama |
| 5,810,807 | A | 9/1998 | Ganz et al. |
| 5,836,947 | A | 11/1998 | Fleischman |
| 5,848,986 | A | 12/1998 | Lundquist et al. |
| 5,865,724 | A | 2/1999 | Palmer et al. |
| 5,897,554 | A | 4/1999 | Chia et al. |
| 5,972,012 | A | 10/1999 | Ream et al. |
| 6,066,102 | A | 5/2000 | Townsend et al. |
| 6,071,277 | A | 6/2000 | Farley et al. |
| 6,074,408 | A | 6/2000 | Freeman |
| 6,093,185 | A | 7/2000 | Ellis et al. |
| 6,093,195 | A | 7/2000 | Ouchi |
| 6,152,918 | A | 11/2000 | Padilla et al. |
| 6,174,280 | B1 | 1/2001 | Oneda et al. |
| 6,203,494 | B1 | 3/2001 | Moriyama |
| 6,352,503 | B1 | 3/2002 | Matsui et al. |
| 6,371,907 | B1 | 4/2002 | Hasegawa et al. |
| 6,395,001 | B1 | 5/2002 | Ellman et al. |
| 6,423,059 | B1 | 7/2002 | Hanson et al. |
| 6,443,943 | B1 | 9/2002 | Ouchi |
| 6,443,944 | B1 | 9/2002 | Doshi et al. |
| 6,450,948 | B1 | 9/2002 | Matsuura et al. |
| 6,451,014 | B1 | 9/2002 | Wakikaido et al. |
| 6,454,703 | B1 | 9/2002 | Ide |
| 6,454,758 | B1 | 9/2002 | Thompson |
| 6,475,222 | B1 | 11/2002 | Berg et al. |
| 6,482,149 | B1 | 11/2002 | Torii |
| 6,488,658 | B1 | 12/2002 | Long |
| 6,500,189 | B1 | 12/2002 | Lang et al. |
| 6,569,105 | B1 | 5/2003 | Kortenbach et al. |
| 6,579,300 | B2 | 6/2003 | Griego et al. |
| 6,602,267 | B2 * | 8/2003 | Castaneda ..................... 606/170 |
| 6,612,992 | B1 | 9/2003 | Hossack et al. |
| 6,663,616 | B1 | 12/2003 | Roth et al. |
| 6,663,625 | B1 | 12/2003 | Ormsby et al. |
| 6,709,388 | B1 | 3/2004 | Mosse et al. |
| 6,730,097 | B2 | 5/2004 | Dennis |
| 6,743,240 | B2 | 6/2004 | Smith et al. |
| 6,764,441 | B2 | 7/2004 | Chiel et al. |
| 6,866,626 | B2 | 3/2005 | Long et al. |
| 7,060,024 | B2 | 6/2006 | Long et al. |
| 7,060,025 | B2 | 6/2006 | Long et al. |
| 7,066,879 | B2 | 6/2006 | Fowler et al. |
| 7,093,518 | B2 | 8/2006 | Gmeilbauer |
| 7,118,587 | B2 * | 10/2006 | Dycus et al. ................ 606/205 |
| 7,799,050 | B2 | 9/2010 | Hensley et al. |
| 2001/0029397 | A1 | 10/2001 | Thompson |
| 2001/0037084 | A1 | 11/2001 | Nardeo |
| 2002/0017515 | A1 | 2/2002 | Obata et al. |
| 2002/0087208 | A1 | 7/2002 | Koblish et al. |
| 2002/0095168 | A1 | 7/2002 | Griego et al. |
| 2002/0120178 | A1 | 8/2002 | Tartaglia et al. |
| 2002/0147445 | A1 | 10/2002 | Farley et al. |
| 2002/0177802 | A1 | 11/2002 | Moutafis et al. |
| 2003/0014051 | A1 | 1/2003 | Woloszko |
| 2003/0032863 | A1 | 2/2003 | Kazakevich |
| 2003/0045778 | A1 | 3/2003 | Ohline et al. |
| 2003/0069474 | A1 | 4/2003 | Couvillon, Jr. |
| 2003/0074014 | A1 * | 4/2003 | Castaneda ..................... 606/167 |
| 2003/0109898 | A1 | 6/2003 | Schwarz et al. |
| 2003/0125788 | A1 | 7/2003 | Long |
| 2003/0153866 | A1 | 8/2003 | Long et al. |
| 2003/0181785 | A1 | 9/2003 | Viebach et al. |
| 2003/0195492 | A1 | 10/2003 | Gobron et al. |
| 2003/0208219 | A1 | 11/2003 | Aznoian et al. |
| 2004/0034343 | A1 | 2/2004 | Gillespie et al. |
| 2004/0044350 | A1 | 3/2004 | Martin et al. |
| 2004/0068291 | A1 | 4/2004 | Suzuki |
| 2004/0092953 | A1 | 5/2004 | Salameh et al. |
| 2004/0097919 | A1 * | 5/2004 | Wellman et al. ............. 606/42 |
| 2004/0143159 | A1 | 7/2004 | Wendlandt |
| 2004/0143160 | A1 | 7/2004 | Couvillon, Jr. |
| 2004/0193016 | A1 | 9/2004 | Root et al. |
| 2004/0204645 | A1 | 10/2004 | Saadat et al. |
| 2004/0230096 | A1 | 11/2004 | Stefanchik et al. |
| 2005/0043743 | A1 | 2/2005 | Dennis |
| 2005/0154164 | A1 | 7/2005 | Tabata |
| 2005/0183733 | A1 | 8/2005 | Kawano et al. |
| 2005/0203610 | A1 | 9/2005 | Tzeng |
| 2005/0222587 | A1 | 10/2005 | Jinno et al. |
| 2005/0234296 | A1 | 10/2005 | Saadat et al. |
| 2005/0272975 | A1 | 12/2005 | McWeeney et al. |
| 2005/0273084 | A1 | 12/2005 | Hinman et al. |
| 2005/0273085 | A1 | 12/2005 | Hinman et al. |
| 2006/0009711 | A1 | 1/2006 | Gingrich et al. |
| 2006/0089627 | A1 | 4/2006 | Burnett et al. |
| 2007/0225562 | A1 | 9/2007 | Spivey et al. |

FOREIGN PATENT DOCUMENTS

| | | |
|---|---|---|
| DE | 19729499 | 1/1999 |
| DE | 19729499 A1 | 1/1999 |
| EP | 0027704 | 4/1981 |
| EP | 0027704 A | 4/1981 |
| EP | 0397489 | 11/1990 |
| EP | 0397489 A1 | 11/1990 |
| EP | 1310206 | 5/2003 |
| EP | 1849421 | 10/2007 |
| JP | 59-181124 | 10/1984 |
| JP | 2004-154164 | 6/2004 |
| JP | 2004 154164 A | 6/2004 |
| WO | 96/10957 | 4/1896 |
| WO | WO 96/00030 | 1/1996 |
| WO | WO 97/12557 | 4/1997 |
| WO | 97/35135 | 9/1997 |
| WO | WO 97/35135 A | 9/1997 |
| WO | 99/12489 | 3/1999 |
| WO | 01/08737 | 2/2001 |
| WO | WO 01/08737 A | 2/2001 |
| WO | 01/82814 | 11/2001 |
| WO | 01/93938 | 12/2001 |
| WO | 02/43797 | 6/2002 |
| WO | 03/053225 | 7/2003 |
| WO | WO 03/053225 A | 7/2003 |
| WO | 03/092476 | 11/2003 |
| WO | 2005/113051 | 12/2005 |
| WO | WO 2005/113051 A | 12/2005 |
| WO | 2006/019291 | 2/2006 |
| WO | WO 2006/019291 A1 | 2/2006 |
| WO | 2006/026687 | 3/2006 |
| WO | 2006/122279 | 11/2006 |
| WO | WO 2006/122279 A | 11/2006 |

OTHER PUBLICATIONS

Brooker, J.C. et al., "A new variable stiffness colonoscope makes colonoscopy easier: a randomised controlled trial," Gut 2000, 46, pp. 801-805 (2000).

Rex, D.K., "Effect of Variable Stiffness Colonoscopes on Cecal Intubation Times for Routine Colonoscopy by an Experienced Examiner in Sedated Patients," Endoscopy; 33 (1), pp. 60-64 (2001).

Shah, S.G., et al., "Magnetic imaging of colonoscopy: an audit of looping, accuracy and ancillary maneuvers," Gastrointestinal Endoscopy, vol. 52, No. 1, pp. 1-8 (2000).

Shah, S.G., et al., "The variable stiffness colonoscope: assessment of efficacy by magnetic endoscope imaging," Gastrointestinal Endoscopy, vol. 56, No. 2, pp. 195-201 (2002).

"Sensors-Resistance," Smart Engineering Group (1999).

European Search Report, European Application No. 07251934 (2 pages) (Aug. 30, 2007).

Exam Report dated Jun. 15, 2010 regarding EP 07251983.8.

EP Search Report dated Jul. 4, 2007, Application No. EP 07 25 1688.

EP Search Report dated Jul. 4, 2007, Application No. EP 07 25 1717.

EP Search Report dated Aug. 3, 2007, Application No. EP 07 25 1683.

EP Search Report dated Aug. 10, 2007, Application No. EP 07 25 2011.

EP Search Report dated Aug. 27, 2007, Application No. EP 07 25 1868.

* cited by examiner

MEDICAL INSTRUMENT HAVING A NEEDLE KNIFE

FIELD OF THE INVENTION

The present invention is related generally to medical equipment, and more particularly to a medical instrument having a needle knife.

BACKGROUND OF THE INVENTION

Endoscopes (including colonoscopes) are known which have an insertion tube which is insertable within a patient. The insertion tube has an articulatable distal end portion controlled by wires running from the distal end portion to control knobs on the handle of the endoscope. A wide angle video camera in the distal end of the insertion tube permits medical observation. In one example, the insertion tube has two working channels. Medical devices, such as a medical needle knife and a medical grasper, are part of an endoscopic system and are insertable into a respective working channel of the insertion tube of the endoscope and are translatable to extend from the distal end portion for medical treatment. Other medical devices are known which use a pull wire to articulate an end effector about a pivot pin.

Still, scientists and engineers continue to seek improved medical instruments having a needle knife.

SUMMARY OF THE INVENTION

A first expression of an embodiment of the invention is for a medical instrument including a flexible sheath, a pivot base, a medical needle knife base, a medical needle knife, and a handpiece. The flexible sheath has a distal sheath portion insertable within a patient and has a proximal sheath portion. The pivot base is attached to the distal sheath portion. The needle knife base is pivotally connected to the pivot base and has a passageway. The medical needle knife is extendable from the passageway and is retractable within the passageway. The handpiece is connected to the proximal sheath portion and includes a manually-operated articulation control operatively connected to the needle knife base for pivoting the needle knife base with respect to the pivot base.

A second expression of an embodiment of the invention is for a medical instrument including a flexible sheath, a pivot base, a medical needle knife base, a medical needle knife, a handpiece, and a lengthwise-translatable articulation cable. The flexible sheath has a distal sheath portion insertable within a patient, has a proximal sheath portion, and has a first lumen. The pivot base is attached to the distal sheath portion. The needle knife base is pivotally connected to the pivot base and has a passageway. The medical needle knife is extendable from the passageway and is retractable within the passageway. The handpiece is connected to the proximal sheath portion and includes a handpiece body, an articulation cam gear, and a manually operated button. The articulation cam gear is pivotally attached to the handpiece body. The button is operatively connected to the articulation cam gear for pivoting the articulation cam gear with respect to the handpiece body. The articulation cable is located in the first lumen and includes a distal cable portion and a proximal cable portion. The distal cable portion is operatively connected to the needle knife base for pivoting the needle knife base with respect to the pivot base upon lengthwise translation of the articulation cable. The proximal cable portion is operatively connected to the articulation cam gear, wherein pivoting of the articulation cam gear lengthwise translates the articulation cable.

A third expression of an embodiment of the invention is for a medical instrument including a flexible sheath, a pivot base, a medical needle knife base, a medical needle knife, and a handpiece. The flexible sheath has a distal sheath portion insertable within a patient, has a proximal sheath portion, and has a first lumen. The pivot base is attached to the distal sheath portion. The needle knife base is pivotally connected to the pivot base and has a passageway. The medical needle knife is extendable from the passageway and is retractable within the passageway. The handpiece is connected to the proximal sheath portion and includes a manually-operated articulation control, a handpiece body, a manually rotatable knob, and a drive shaft. The articulation control is operatively connected to the needle knife base for pivoting the needle knife base with respect to the pivot base. The handpiece body has a proximal body end portion. The knob is located at the proximal body end portion. The drive shaft is located within the handpiece body, has a distal drive shaft portion attached to the proximal sheath portion, and has a proximal drive shaft portion attached to the knob, wherein rotation of the knob with respect to the handpiece body rotates the drive shaft which rotates the flexible sheath which rotates the pivot base.

Several benefits and advantages are obtained from one or more of the expressions of an embodiment of the invention. In a first example, the flexible sheath is inserted into a working channel of a flexible insertion tube of an endoscope, wherein the needle knife base (and hence the medical needle knife) can be articulated with respect to the endoscope insertion tube allowing independent alignment of the medical needle knife with respect to the wide angle video camera of the endoscope and, for example, a medical grasper extended from a second working channel of the endoscope insertion tube. In a second example, the flexible sheath and/or the pivot base has a sheath and/or base-to-endoscope-rail feature allowing the flexible sheath and/or pivot base to be coupled to, and slid along, an exterior rail of a flexible insertion tube of an endoscope allowing independent alignment of the medical needle knife with respect to the wide angle video camera of the endoscope and, for example, a medical grasper extended from a working channel of the endoscope insertion tube. In one variation, the needle knife base is articulatable and rotatable with the medical needle knife being translatable to extend from and to be retracted within the passageway of the needle knife base.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiment of the present invention for the convenience of the reader and are not for the purpose of limiting the invention.

It is understood that any one or more of the following-described expressions of an embodiment, examples, etc. can be combined with any one or more of the other following-described expressions of an embodiment, examples, etc.

Figure 1:
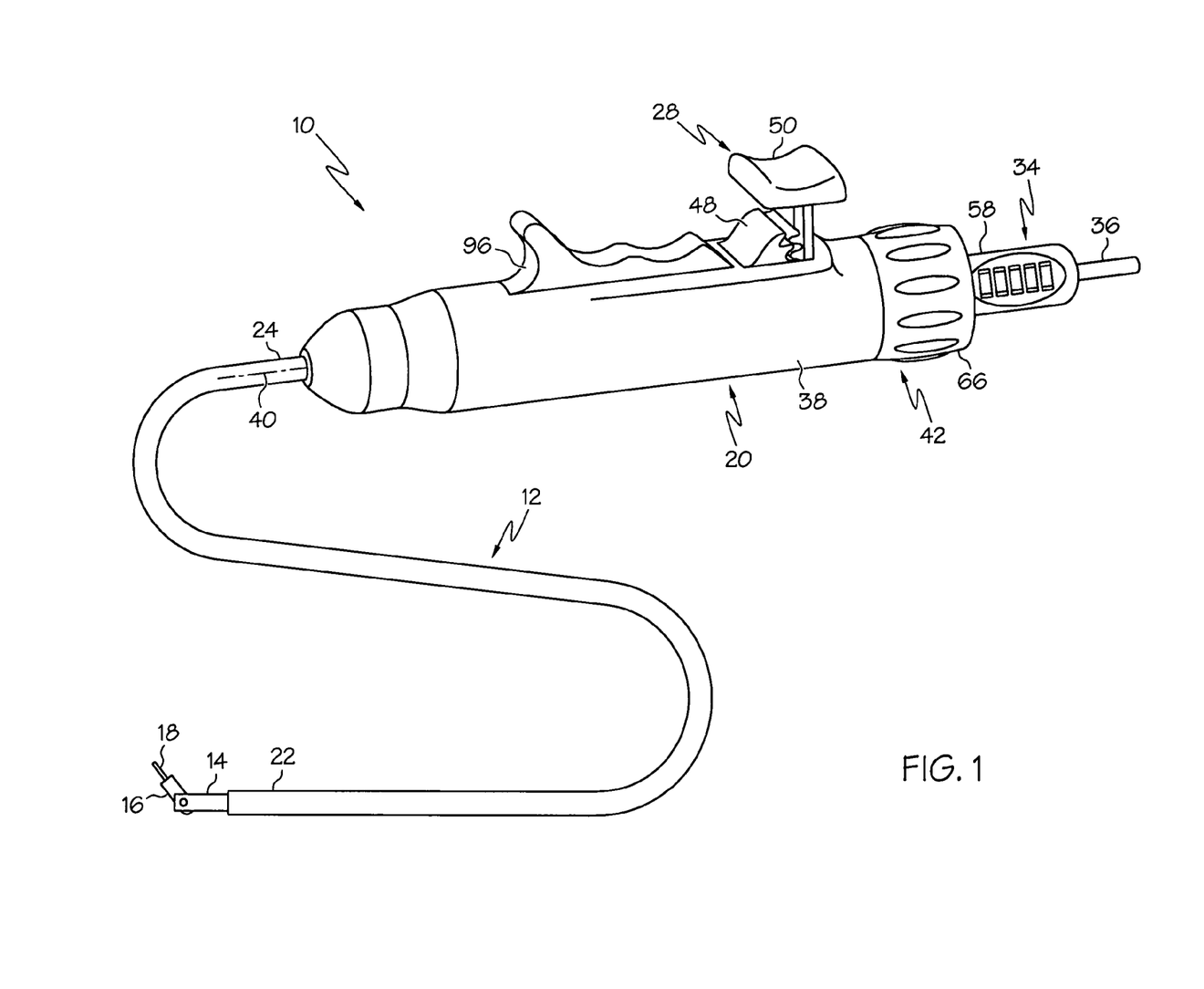
FIG. 1 is a schematic perspective side view of an embodiment of the medical instrument of the invention.
Figure 2:
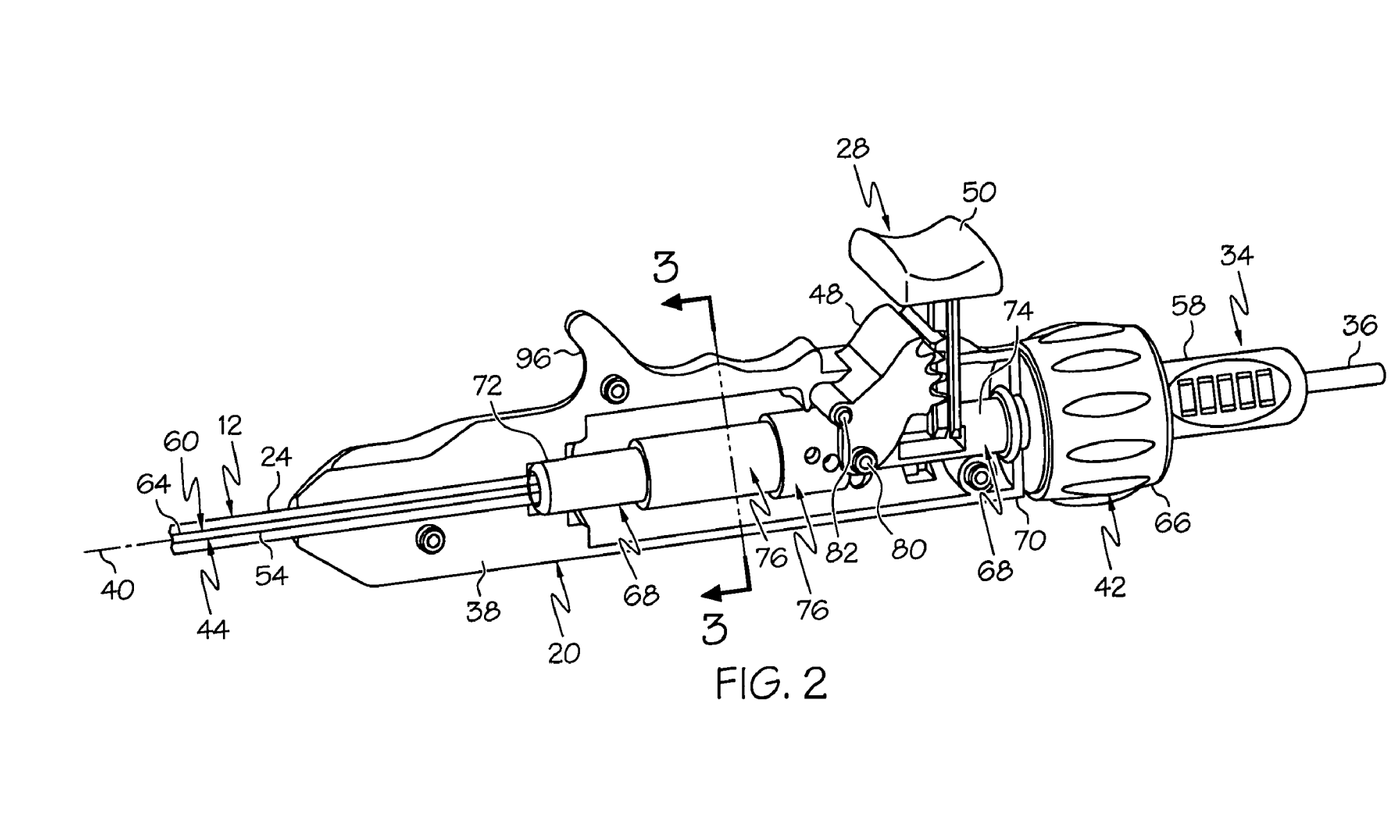
FIG. 2 is a view of the proximal portion of the medical instrument of FIG. 1 with a half of the two-piece handpiece body removed and with the flexible sheath shown in cross section.
Figure 3:
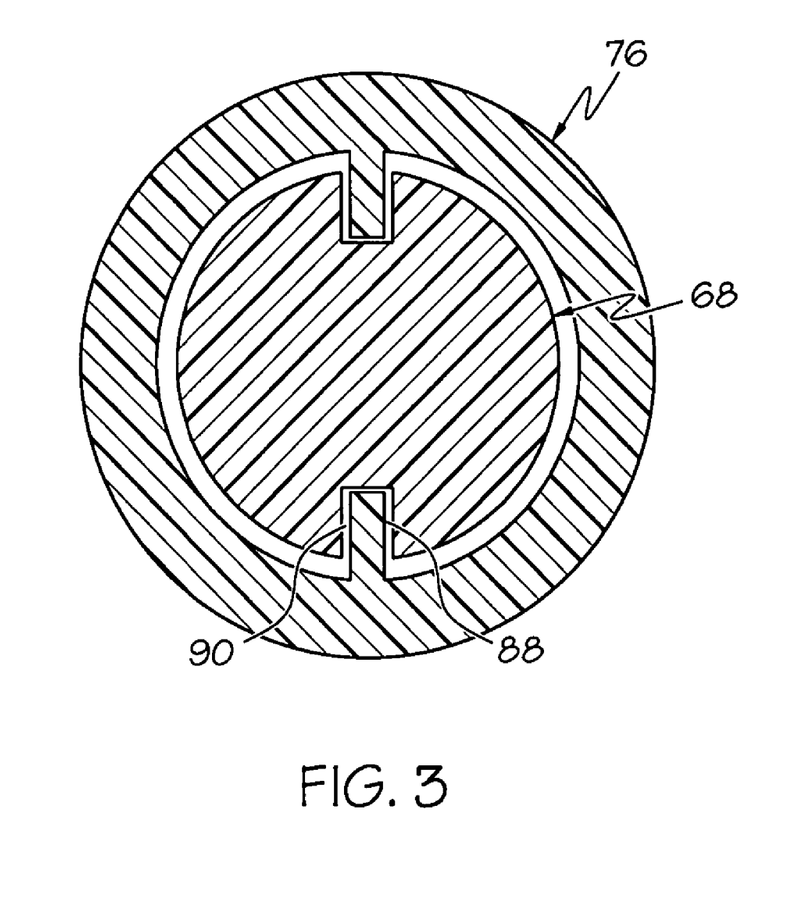
FIG. 3 is a cross sectional view of the rotation coupler and the drive shaft of FIG. 2 taken along lines 3-3 of FIG. 2.
Figure 4:
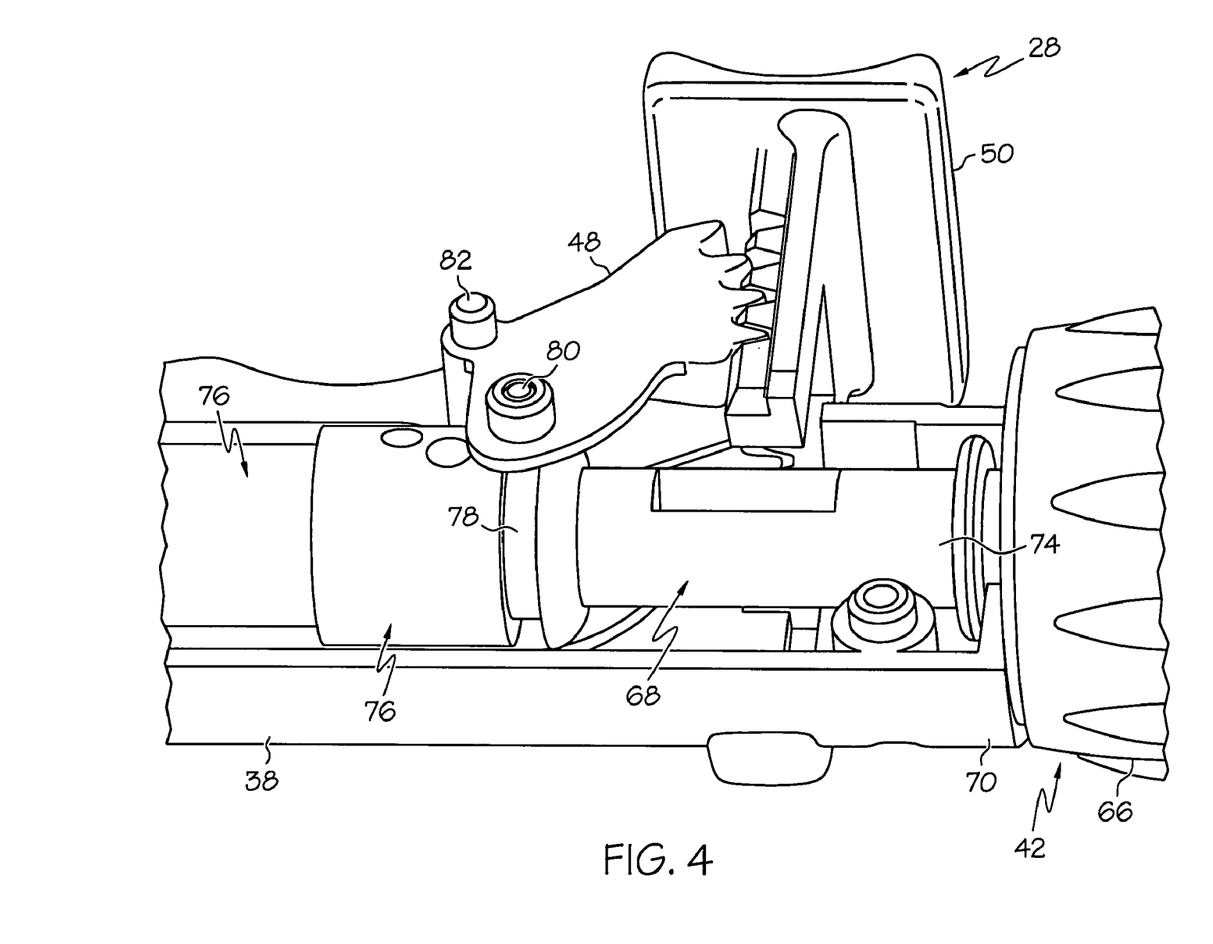
FIG. 4 is a bottom side perspective view of a portion of the handpiece of FIG. 2.
Figure 5:
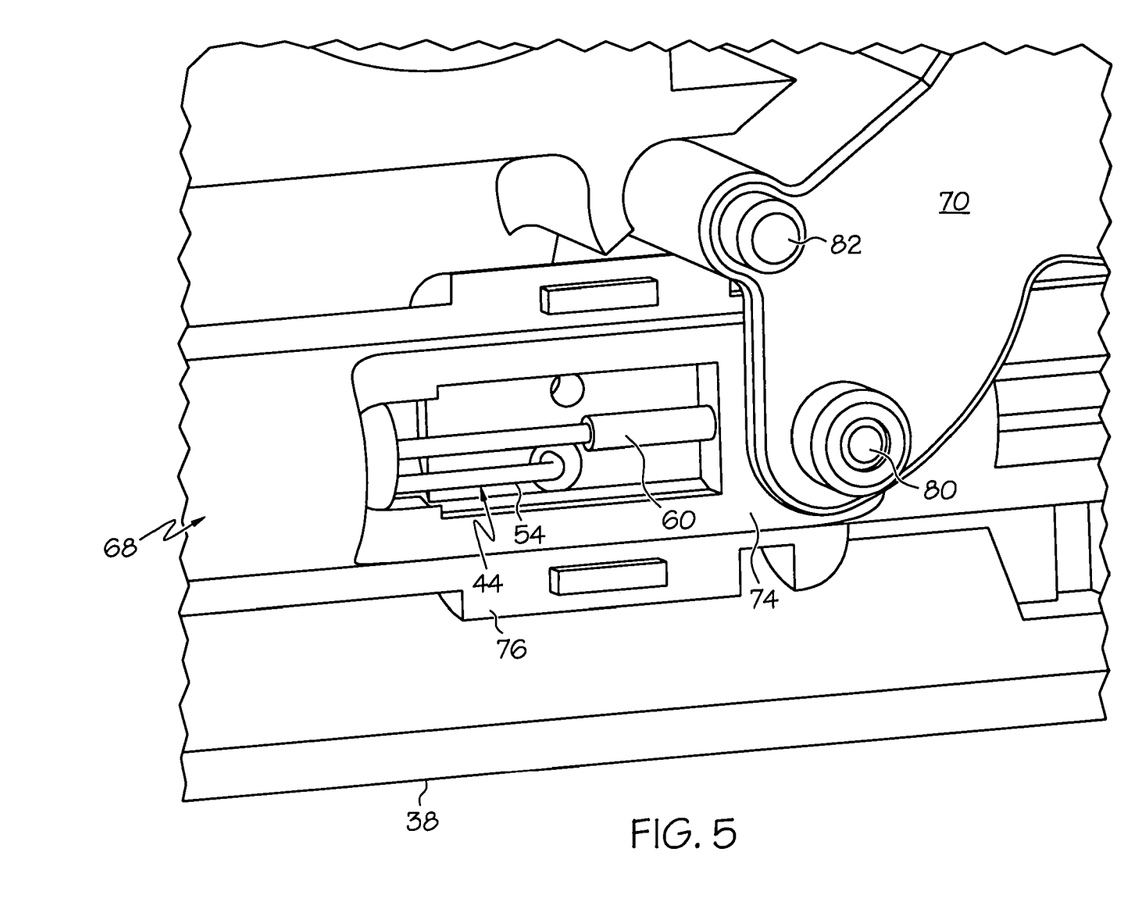
FIG. 5 is an enlarged view of a portion of the medical instrument of FIG. 2.
Figure 6:
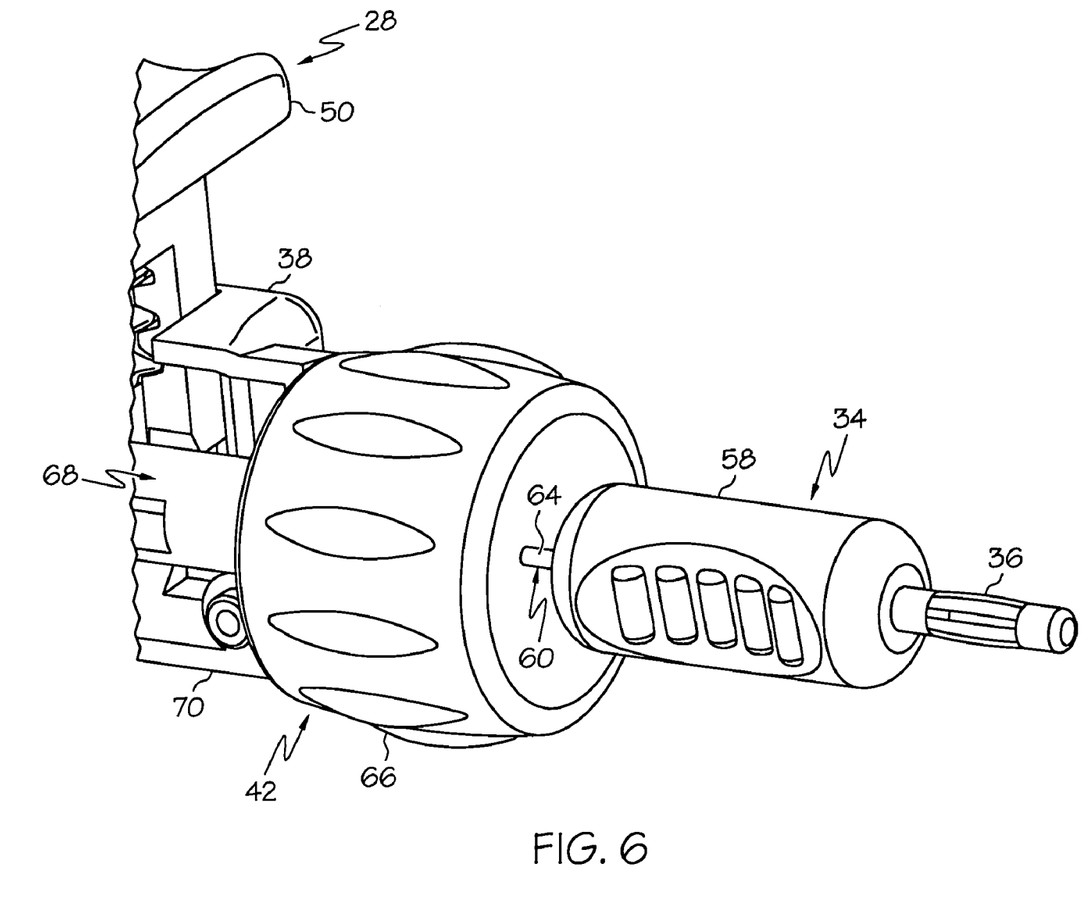
FIG. 6 is a perspective rear view of a portion of the handpiece of the medical instrument of FIG. 2.
Figure 7:
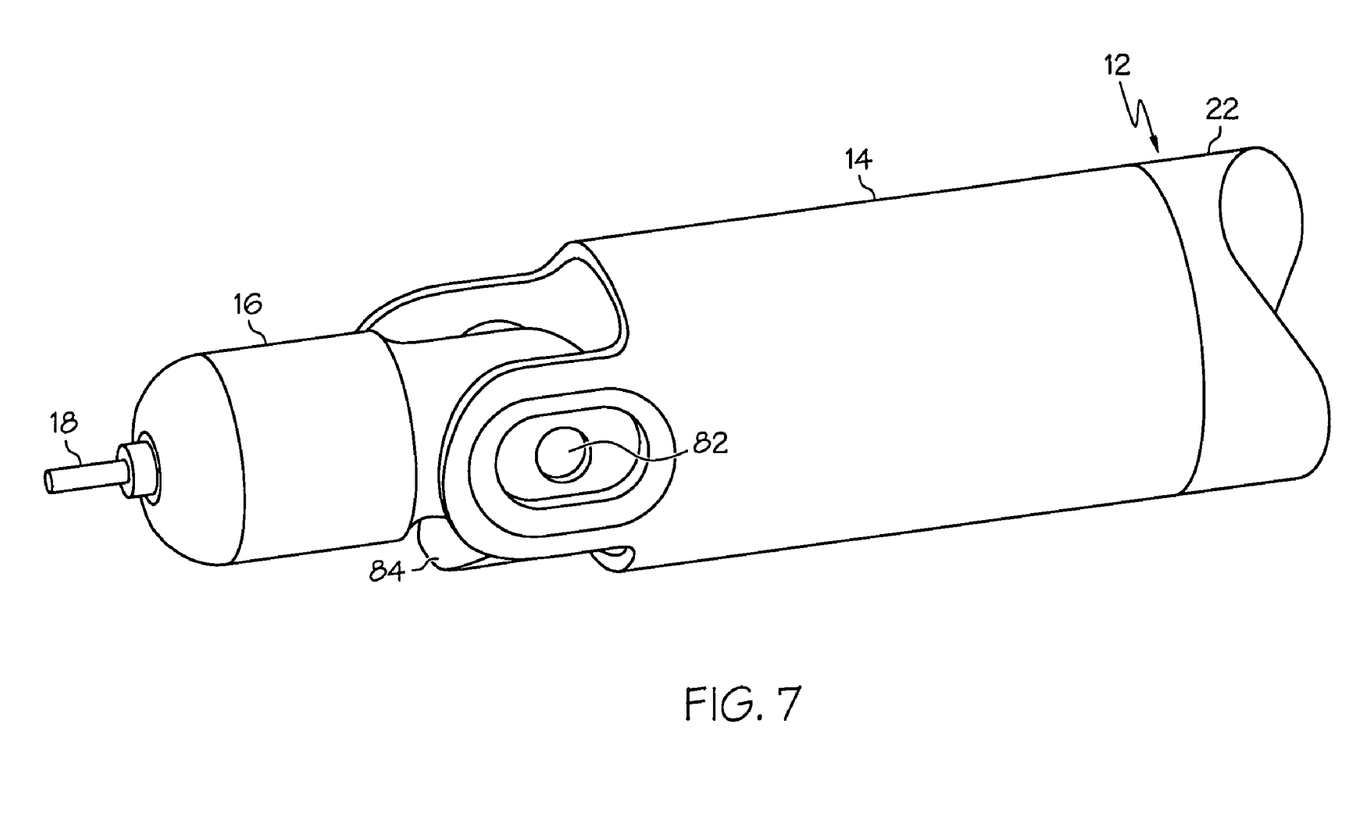
FIG. 7 is an enlarged perspective view of the distal portion of the medical instrument of FIG. 1.
Figure 8:
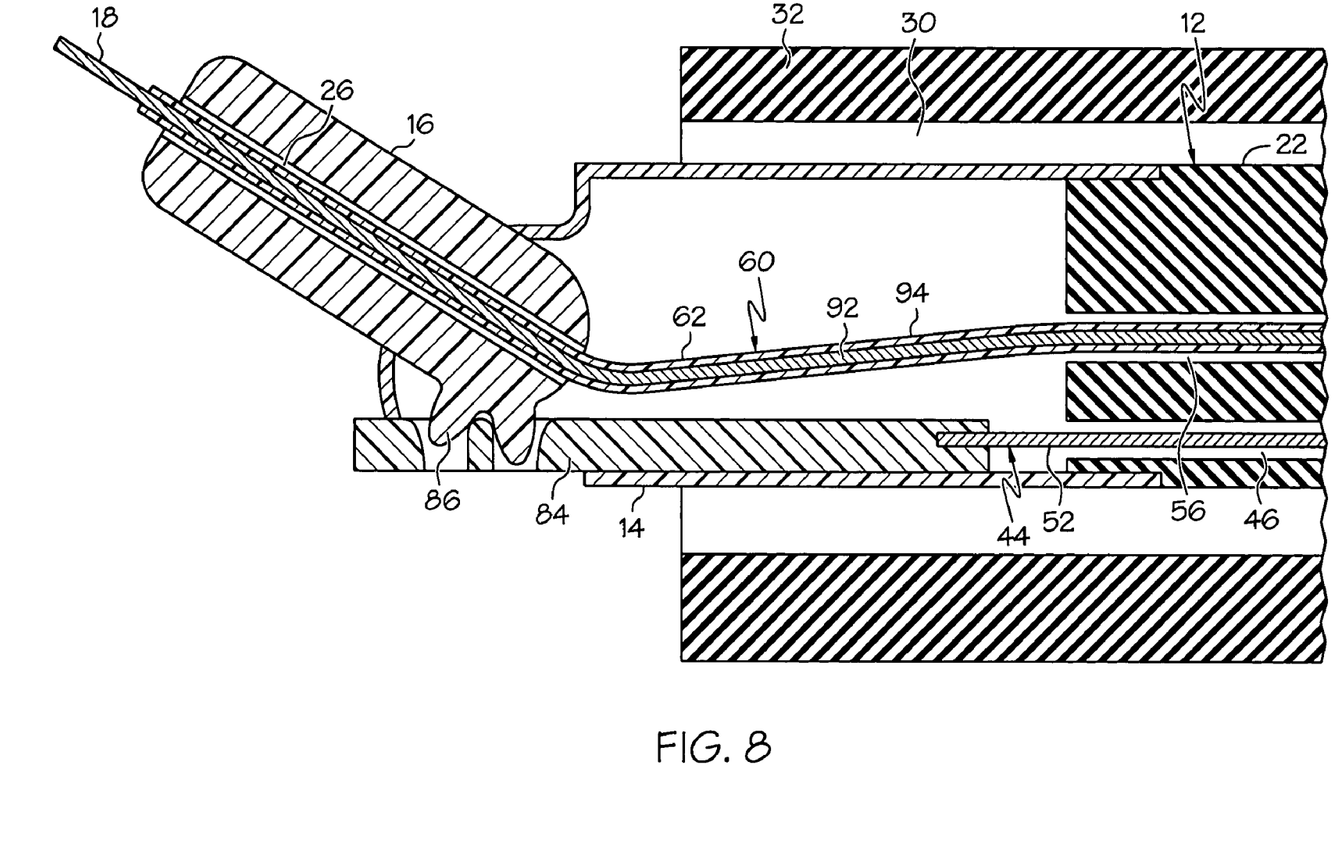
FIG. 8 is a side elevational, cross sectional view of the distal portion of the medical instrument of FIG. 7 shown extending from a working channel of an endoscope insertion tube.
Figure 9:
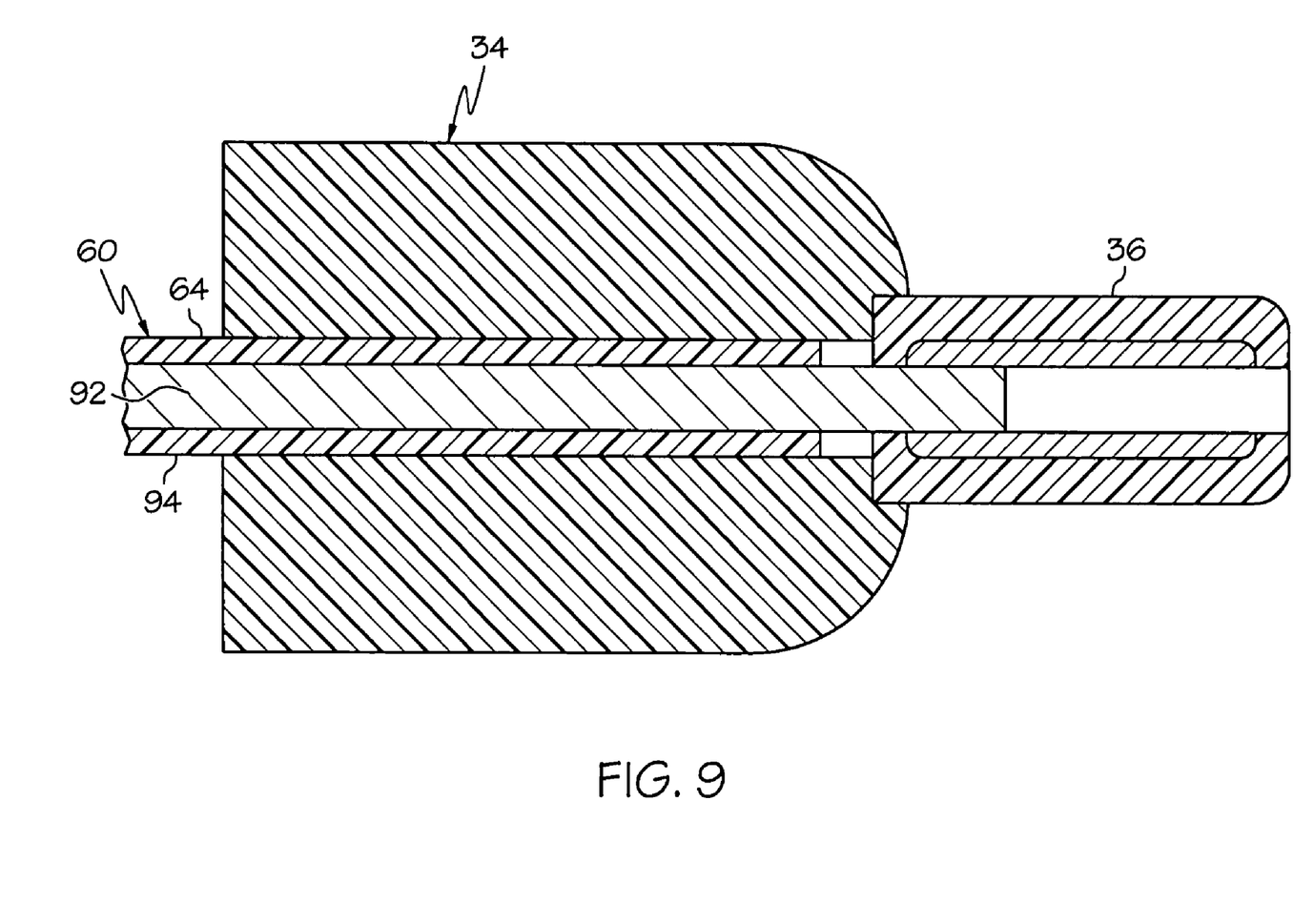
FIG. 9 is a cross sectional schematic view of the needle knife handle and the electrical connector of the medical instrument of FIG. 1.

Referring now to the Figures, wherein like numerals represent like elements throughout, FIGS. 1-8 illustrate an embodiment of the invention. A first expression of the embodiment of FIGS. 1-8 is for a medical instrument 10 including a flexible sheath 12, a pivot base 14, a medical needle knife base 16, a medical needle knife 18, and a handpiece 20. The flexible sheath 12 has a distal sheath portion 22 insertable within a patient and has a proximal sheath portion 24. The pivot base 14 is attached to the distal sheath portion 22. The needle knife base 16 is pivotally connected to the pivot base 14 and has a passageway 26. The medical needle knife 18 is extendable from the passageway 26 and is retractable within the passageway 26. The handpiece 20 is connected to the proximal sheath portion 24 and includes a manually-operated articulation control 28 operatively connected to the needle knife base 16 for pivoting the needle knife base 16 with respect to the pivot base 14.

In one application of the first expression of the embodiment of FIGS. 1-8, the needle knife base 16, the pivot base 14, and the distal sheath portion 22 are insertable within a working channel 30 of a flexible endoscope insertion tube 32.

In one enablement of the first expression of the embodiment of FIGS. 1-8, the handpiece 20 includes a manually-operated translation control 34 operatively connected to the medical needle knife 18 for extending the medical needle knife 18 from the passageway 26 and for retracting the medical needle knife 18 within the passageway 26. In one variation, the handpiece 20 includes an electrical connector 36 electrically connected to the medical needle knife 18. In one modification, the handpiece 20 includes a handpiece body 38, and the proximal sheath portion 24 has a centerline 40 and is rotatable with respect to the handpiece body 38 about the centerline 40. In one example, the handpiece 20 includes a manually-operated rotation control 42 operatively connected to the proximal sheath portion 24 for rotating the proximal sheath portion 24 with respect to the handpiece body 38 about the centerline 40.

In one arrangement of the first expression of the embodiment of FIGS. 1-8, the medical needle knife 18 is electrically energizable (such as via an electrical connector 36), and the needle knife base 16 is not electrically energizable by the medical needle knife 18. Having the needle knife base 16 not be electrically energizable by the medical needle knife 18 can be accomplished in a variety of ways such as, without limitation, by having the needle knife base 16 be an electrically-insulative base, by having the needle knife base 16 be an electrically-conductive base having an electrically-insulative coating at least surrounding the passageway 26, or by having the needle knife base 16 be an electrically-conductive base and having the medical needle knife 18 be surrounded by electrical insulation 94 except for its uninsulated distal tip wherein, when the uninsulated distal tip is withdrawn into the passageway 26, there is always an insulating air gap in the passageway 26 between the uninsulated distal tip and the wall of the needle knife base 16 surrounding the passageway 26.

A second expression of the embodiment of FIGS. 1-8 is for a medical instrument 10 including a flexible sheath 12, a pivot base 14, a medical needle knife base 16, a medical needle knife 18, a handpiece 20, and a lengthwise-translatable articulation cable 44. The flexible sheath 12 has a distal sheath portion 22 insertable within a patient, has a proximal sheath portion 24, and has a first lumen 46. The pivot base 14 is attached to the distal sheath portion 22. The needle knife base 16 is pivotally connected to the pivot base 14 and has a passageway 26. The medical needle knife 18 is extendable from the passageway 26 and is retractable within the passageway 26. The handpiece 20 is connected to the proximal sheath portion 24 and includes a handpiece body 38, an articulation cam gear 48, and a manually operated button 50. The articulation cam gear 48 is pivotally attached to the handpiece body 38. The button 50 is operatively connected to the articulation cam gear 48 for pivoting the articulation cam gear 48 with respect to the handpiece body 38. The articulation cable 44 is located in the first lumen 46 and includes a distal cable portion 52 and a proximal cable portion 54. The distal cable portion 52 is operatively connected to the needle knife base 16 for pivoting the needle knife base 16 with respect to the pivot base 14 upon lengthwise translation of the articulation cable 44. The proximal cable portion 54 is operatively connected to the articulation cam gear 48, wherein pivoting of the articulation cam gear 48 lengthwise translates the articulation cable 44.

It is noted that the term "cable" includes any elongated member. In one choice of materials, the articulation cable 44 comprises, consists essentially of, or consists of nitinol. It is also noted that the applications, variations, modifications, and examples of the first expression of the embodiment of FIGS. 1-8 are equally applicable to the second expression of the embodiment of FIGS. 1-8. In one example, the button 50 is a spring biased button.

In one enablement of the second expression of the embodiment of FIGS. 1-8, the flexible sheath 12 has a second lumen 56, and the handpiece 20 includes a manually translatable needle knife handle 58. In one variation, the medical instrument 10 also includes an activation wire 60 disposed in the second lumen 56 and having a distal wire portion 62 and a proximal wire portion 64. In one modification, the distal wire portion 62 is attached to the medical needle knife 18, and the proximal wire portion 64 is attached to a needle knife handle 58. In one example, the distal wire portion 62 is monolithically attached to the medical needle knife 18. Thus, in this example, the distal wire portion 62 and the medical needle knife 18 are two portions of one continuous piece. In one illustration, the activation wire 60 and the medical needle knife 18 are two portions of one continuous piece.

It is noted that the term "wire" includes any elongated member. In one choice of materials, the activation wire 60 (or the conductor portion thereof) comprises, consists essentially of, or consists of nitinol.

A third expression of the embodiment of FIGS. 1-8 is for a medical instrument 10 including a flexible sheath 12, a pivot base 14, a medical needle knife base 16, a medical needle knife 18, and a handpiece 20. The flexible sheath 12 has a distal sheath portion 22 insertable within a patient, has a proximal sheath portion 24, and has a first lumen 46. The pivot base 14 is attached to the distal sheath portion 22. The needle knife base 16 is pivotally connected to the pivot base 14 and has a passageway 26. The medical needle knife 18 is extendable from the passageway 26 and is retractable within the passageway 26. The handpiece 20 is connected to the proximal sheath portion 24 and includes a manually-operated articulation control 28, a handpiece body 38, a manually rotatable knob 66, and a drive shaft 68. The articulation control 28 is operatively connected to the needle knife base 16 for pivoting the needle knife base 16 with respect to the pivot base 14. The handpiece body 38 has a proximal body end portion 70. The knob 66 is disposed at the proximal body end portion 70. The drive shaft 68 is disposed within the handpiece body 38, has a distal drive shaft portion 72 attached to the proximal sheath portion 24, and has a proximal drive shaft portion 74 attached to the knob 66, wherein rotation of the knob 66 with respect to the handpiece body 38 rotates the drive shaft 68 which rotates the flexible sheath 12 which rotates the pivot base 14.

It is noted that the applications and variations of the first expression of the embodiment of FIGS. 1-8 and the enablements, variations, modifications and examples of the second expression of the embodiment of FIGS. 1-8 are equally applicable to the third expression of the embodiment of FIGS. 1-8.

In one enablement of the third expression of the embodiment of FIGS. 1-8, the medical instrument 10 also includes an articulation cam gear 48, a manually operated button 50, and a lengthwise-translatable articulation cable 44. The articulation cam gear 48 is pivotally attached to the handpiece body 38. The button 50 is operatively connected to the articulation cam gear 48 for pivoting the articulation cam gear 48 with respect to the handpiece body 38. The articulation cable 44 is disposed in the first lumen 46 and includes a distal cable portion 52 and a proximal cable portion 54. The distal cable portion 52 is operatively connected to the needle knife base 16 for pivoting the needle knife base 16 with respect to the pivot base 14 upon lengthwise translation of the articulation cable 44. The proximal cable portion 54 is operatively connected to the articulation cam gear 48, wherein pivoting of the articulation cam gear 48 lengthwise translates the articulation cable 44.

In one implementation of the third expression of the embodiment of FIGS. 1-8, the medical instrument 10 also includes a rotation coupler 76 disposed within the handpiece body 38, surrounding the drive shaft 68, lengthwise translatable with respect to the drive shaft 68, and non-rotatable with respect to the drive shaft 68. The proximal cable portion 54 is attached to the rotation coupler 76, and the rotation coupler 76 has a circumferential notch 78. The articulation cam gear 48 has a pin 80 which engages the notch 78, wherein pivoting of the articulation cam gear 48 lengthwise translates the rotation coupler 76 with respect to the drive shaft 68 which lengthwise translates the articulation cable 44 with respect to the flexible sheath 12.

In one example, not shown, of the embodiment of the medical instrument 10 of FIGS. 1-8, the pivot base 14 is adapted to be coupled to, and slid along, an exterior rail of a flexible endoscope insertion tube 32. In one procedure, the needle knife handle 58 is pulled to retract the medical needle knife 18 within the passageway 26. Then, the needle knife base 16 is coupled to the exterior rail of an endoscope insertion tube 32 whose distal end has been positioned within a patient at a tissue site requiring medical treatment. Then, the flexible sheath 12 is pushed sliding the needle knife base 16 to the distal end of the endoscope insertion tube 32. At some point, a medical grasper, not shown, has been inserted into a working channel 30 of the endoscope insertion tube 32 and translated to extend from the distal end of the endoscope insertion tube 32, wherein the endoscope insertion tube 32 has been articulated to align the medical grasper. Then, the needle-knife handle 58 is pushed to extend the medical needle knife 18 from the passageway 26, wherein the button 50 has been pushed and/or the knob 66 has been rotated to align the medical needle knife 18 independently of the alignment of the medical grasper. The medical needle knife 18 is then used to treat the patient tissue.

In another procedure, the needle knife base 16, the pivot base 14 and the distal sheath portion 22 are inserted into a first working channel of a flexible endoscope insertion tube, and the medical grasper is inserted into a second working channel (not shown) of the endoscope insertion tube. Other endoscope and non-endoscope procedures which use the embodiment of the medical instrument 10 of FIGS. 1-8 are left to those skilled in the art.

In one construction of the embodiment of FIGS. 1-8, pivot pins 82 for pivotal connections are provided as shown in the figures. In one variation, the electrical connector 36 is a banana plug. In one modification, the distal cable portion 52 is attached to a rack 84 disposed in the pivot base 14, and the needle knife base 16 includes pinion teeth 86 operatively engaging the rack 84, wherein lengthwise translation of the articulation cable 44 translates the rack 84 which articulates the needle knife base 16 with respect to the pivot base 14 about the pivot pin 82 associated with the needle knife base 16. In one example, the rotation coupler 76 includes inwardly extending ribs 88 which slidingly engage surface grooves 90 in the drive shaft 68 to allow lengthwise translation of the rotation coupler 76 with respect to the drive shaft 68 while preventing rotation of the rotation coupler 76 with respect to the drive shaft 68. Thus, the articulation cable 44 will not be twisted when the knob 66 is rotated to rotate the drive shaft 68 and hence the needle knife base 16. In one employment, the activation wire 60 is electrically isolated from the patient when the medical needle knife 18 is retracted within the passageway 26, such as from wire insulation and/or surrounding insulative structure. In one configuration, the activation wire 60 includes an electrical conductor 92 surrounded by electrical insulation 94. In one design, the handpiece 20 includes a finger support 96.

Several benefits and advantages are obtained from one or more of the expressions of an embodiment of the invention. In a first example, the flexible sheath is inserted into a working channel of a flexible insertion tube of an endoscope, wherein the needle knife base (and hence the medical needle knife) can be articulated with respect to the endoscope insertion tube allowing independent alignment of the medical needle knife with respect to the wide angle video camera of the endoscope and, for example, a medical grasper extended from a second working channel of the endoscope insertion tube. In a second example, the flexible sheath and/or the pivot base has a sheath and/or base-to-endoscope-rail feature allowing the flexible sheath and/or pivot base to be coupled to, and slid along, an exterior rail of a flexible insertion tube of an endoscope allowing independent alignment of the medical needle knife with respect to the wide angle video camera of the endoscope and, for example, a medical grasper extended from a working channel of the endoscope insertion tube. In one variation, the needle knife base is articulatable and rotatable with the medical needle knife being translatable to extend from and to be retracted within the passageway of the needle knife base.

While the present invention has been illustrated by a description of several expressions of an embodiment, it is not the intention of the applicants to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended Claims.

What is claimed is:

1. A medical instrument comprising:
   a) a flexible sheath having a distal sheath portion insertable within a patient, having a proximal sheath portion, and having a first lumen, wherein the distal sheath portion has a distal end;
   b) a pivot base fixedly attached to the distal sheath portion;
   c) a medical needle knife base pivotally connected to the pivot base and having a passageway;
   d) a medical needle knife extendable from the passageway and retractable within the passageway, wherein the medical needle knife is extendable distally beyond the distal end of the distal sheath portion; and
   e) a handpiece connected to the proximal sheath portion and including:
      (1) a manually-operated articulation control operatively connected to the needle knife base for pivoting the needle knife base with respect to the pivot base without translating the sheath with respect to the handpiece;
      (2) a manually-operated translation control operatively connected to the medical needle knife for extending the medical needle knife from the passageway and for retracting the medical needle knife within the passageway, wherein the translation control is a separate and independent control from the articulation control;
      (3) a handpiece body having a proximal body end portion, wherein the sheath has an exposed outer surface from the handpiece to the pivot base;
      (4) a manually rotatable knob disposed at the proximal body end portion; and
      (5) a drive shaft disposed within the handpiece body, having a distal drive shaft portion attached to the proximal sheath portion, and having a proximal drive shaft portion attached to the knob, wherein rotation of the knob with respect to the handpiece body rotates the drive shaft which rotates the flexible sheath which rotates the pivot base;
   f) the handpiece further including:
      (1) an articulation cam gear pivotally attached to the handpiece body;
      (2) a manually operated button operatively connected to the articulation cam gear for pivoting the articulation cam gear with respect to the handpiece body; and
      (3) a lengthwise-translatable articulation cable disposed in the first lumen, having a distal cable portion operatively connected to the needle knife base for pivoting the needle knife base with respect to the pivot base upon lengthwise translation of the articulation cable, and having a proximal cable portion operatively connected to the articulation cam gear, wherein pivoting of the articulation cam gear lengthwise translates the articulation cable;
      (4) a rotation coupler disposed within the handpiece body, surrounding the drive shaft, lengthwise translatable with respect to the drive shaft, and non-rotatable with respect to the drive shaft, wherein the proximal cable portion is attached to the rotation coupler, wherein the rotation coupler has a circumferential notch, wherein the articulation cam gear has a pin which engages the notch, and wherein pivoting of the articulation cam gear lengthwise translates the rotation coupler with respect to the drive shaft which lengthwise translates the articulation cable with respect to the flexible sheath.

2. The medical instrument of claim 1, wherein the flexible sheath has a second lumen, wherein the handpiece includes a manually translatable needle knife handle, and also including an activation wire disposed in the second lumen and having a distal wire portion and a proximal wire portion, wherein the distal wire portion is attached to the medical needle knife, and wherein the proximal wire portion is attached to a needle knife handle.

3. The medical instrument of claim 2, wherein the distal wire portion is monolithically attached to the medical needle knife.

4. The medical instrument of claim 2, also including an electrical connector attached to the needle knife handle and electrically connected to the proximal wire portion.

* * * * *